(12) United States Patent
Matsuura et al.

(10) Patent No.: US 10,695,392 B2
(45) Date of Patent: Jun. 30, 2020

(54) ORAL COMPOSITION FOR IMPROVING SYSTEMIC SYMPTOMS INCLUDING SENSITIVITY TO COLD

(71) Applicant: SSP CO. LTD, Tokyo (JP)

(72) Inventors: Kentaro Matsuura, Ingelheim am Rhein (DE); Ichiro Kawase, Ingelheim am Rhein (DE); Atsushi Sawamura, Ingelheim am Rhein (DE)

(73) Assignee: SSP CO. LTD, Tokyo (JP)

( * ) Notice: Subject to any disclaimer, the term of this patent is extended or adjusted under 35 U.S.C. 154(b) by 0 days.

(21) Appl. No.: 15/313,144

(22) PCT Filed: May 22, 2015

(86) PCT No.: PCT/EP2015/061453
§ 371 (c)(1),
(2) Date: Nov. 22, 2016

(87) PCT Pub. No.: WO2015/181096
PCT Pub. Date: Dec. 3, 2015

(65) Prior Publication Data
US 2017/0202899 A1    Jul. 20, 2017

(30) Foreign Application Priority Data

May 27, 2014 (JP) ................................. 2014-108649

(51) Int. Cl.
| | | |
|---|---|---|
| *A61K 36/87* | (2006.01) | |
| *A61K 9/00* | (2006.01) | |
| *A61K 47/02* | (2006.01) | |
| *A61K 47/26* | (2006.01) | |

(52) U.S. Cl.
CPC ............ *A61K 36/87* (2013.01); *A61K 9/0053* (2013.01); *A61K 47/02* (2013.01); *A61K 47/26* (2013.01)

(58) Field of Classification Search
None
See application file for complete search history.

(56) References Cited

U.S. PATENT DOCUMENTS

| | | |
|---|---|---|
| 2004/0151769 A1 | 8/2004 | Esperester |
| 2004/0151794 A1* | 8/2004 | Sacher ............ A61K 36/87 424/774 |
| 2005/0038125 A1 | 2/2005 | Smit |
| 2005/0142235 A1 | 6/2005 | Horie |
| 2005/0202110 A1* | 9/2005 | Horie ............ A61K 31/355 424/774 |
| 2009/0162457 A1 | 6/2009 | Minegishi |

FOREIGN PATENT DOCUMENTS

| | | |
|---|---|---|
| CN | 1901929 A | 1/2007 |
| CN | 101296693 A | 10/2008 |
| CN | 103635185 A | 3/2014 |
| EP | 1435242 A1 | 7/2004 |
| EP | 1550452 A1 | 7/2005 |
| JP | 2003146895 A | 5/2003 |
| JP | 2005052085 A | 3/2005 |
| JP | 2006513263 A | 4/2006 |
| JP | 2006516542 A | 7/2006 |
| JP | 2007145809 A | 6/2007 |
| JP | 2007516991 A | 6/2007 |
| JP | 2007516992 A | 6/2007 |
| JP | 2009023922 A | 2/2009 |
| JP | 2012240956 A | 12/2012 |
| WO | 2004058227 A1 | 7/2004 |

OTHER PUBLICATIONS

Keisewetter et al. (2000) Arzneimittelforschung 50(20): 109-117.*
Schaefer et al. (2003) Arzneimittelforschung 53(4): 243-246.*
Rabe et al. (2011) Eur. J. Vasc. Endovasc. Surg. 41: 540-547.*
Van Uden et al. (2005) Clinical Rehabilitation 19: 339-344.*
International Search Report for corresponding PCT Application No. PCT/EP2015/061453, 3 pages, dated Jul. 21, 2015.
A pamphlet of Antistax (SSP Co . , Ltd.,) 2 pages.
Ariga Toshiaki: "The antioxidative function. preventive action on disease and utilization of proanthocyanidins" Biofactors, vol. 21. No. 1-4, pp. 197-201, Jan. 2004.
Sophie La Fay et al: "Grape extract improves antioxidant status and physical performance in elite male athletes". Journal of Sports Science & Medicine vol. 8. No. 3, 13 pages, pp. 468-480, Jan. 1, 2009.
Schaefer Eckhard et al: "Oedema protective properties of the red vine leaf extract AS 195 (*Folia vitis* viniferae) in the treatment of chronic venous insufficiency. A 6-week observational clinical trial", Arzneimittel-Forschung 2003, vol. 53. No. 4. pp. 243-246, Jan. 2003.
Office Action for corresponding Chinese Patent Application No. 201580027922.4, 35 pages, dated Mar. 4, 2019.
Yoshihiko Minegishi, et al., "Red grape leaf extract improves endurance capacity by facilitating fatty acid utilization in skeletal muscle in mice" Eur J Appl Physiol 111: pp. 1983-1989, Jan. 20, 2011.
Tong Xin, "Red Vine Leaf Improves Venous Insufficiency" Foreign Medicine (volume of TCM &Chinese herbal), vol. 23, pp. 189-190, Jun. 15, 2001 (for relevancy see Office Action for corresponding Chinese Patent Application No. 201580027922.4, cited above).
Hideaki Shimizu, Junkan Plus, vol. 14, No. 10, pp. 10-12, (Aug. 2014).
Akio Nakajma, Journal of Clinical Rehabilitation, vol. 9, No. 8, pp. 806-810, (Aug. 2014).

(Continued)

*Primary Examiner* — Terry A McKelvey
*Assistant Examiner* — Russell G Fiebig
(74) *Attorney, Agent, or Firm* — Matthew B. Dernier, Esq.

(57) ABSTRACT

Disclosed embodiments provide a method of improving systemic symptoms such as sensitivity to cold via an oral composition. The oral composition includes, as its effective component, a red vine leaf extract to improve a symptom selected from the group consisting of sensitivity to cold, general fatigue, general weariness, stiff shoulders, and neck stiffness.

4 Claims, 2 Drawing Sheets

(56) References Cited

OTHER PUBLICATIONS

Ito, et al., Japan Medical Journal, No. 4781, pp. 18-23, (Dec. 12, 2015).
Kampo & the newest therapy, 23 (2) pp. 127-134, (May 2014) [for relevancy see English abstract at end of the document].
Health Life Business, No. 547, 1 page (Oct. 1, 2012) (for relevancy see Official Notification cited below).
Product Catalog "Dried wine grape leaf extracts 085. 266&085. 945", Ask Intercity Co., Ltd. 3 pages (Apr. 6, 2004) (for relevancy see Official Notification cited below).
Resveratrol Catalog Ver. 2. 4SJ, Oryza Oil & Fat Chemical Co., Ltd., Date of enactment: Sep. 14, 2007, Date of revision: (Mar. 6, 2012) (for relevancy see Official Notification cited below).
Notification re corresponding JP 2016-567067, 31 pages, dated Aug. 7, 2018 (with a partial translation).
Office Action issued for corresponding Japanese Patent Application No. 2016-567067, 13 pages, dated Mar. 5, 2019.
Ireneusz Chrzascik: "Analysis of Biologically Active Stilbene Derivatives" Critical Reviews in Analytical Chemistry, 2009, vol. 39, pp. 70-80 (2009) (for relevancy see Office Action issued for corresponding Japanese Patent Application No. 2016-567067 cited above).
Tsuboi Sincerity Makoto Tsuboi, "working effect of special edition/ physiological active substance and effect", Fragrance Journal No. 88 vol. 16, No. 1 (1988) (for relevancy see Office Action issued for corresponding Japanese Patent Application No. 2016-567067 cited above).
Office Action for corresponding Mexican Patent Application No. MX/a/2016/015423, 10 pages dated Mar. 3, 2020.

\* cited by examiner

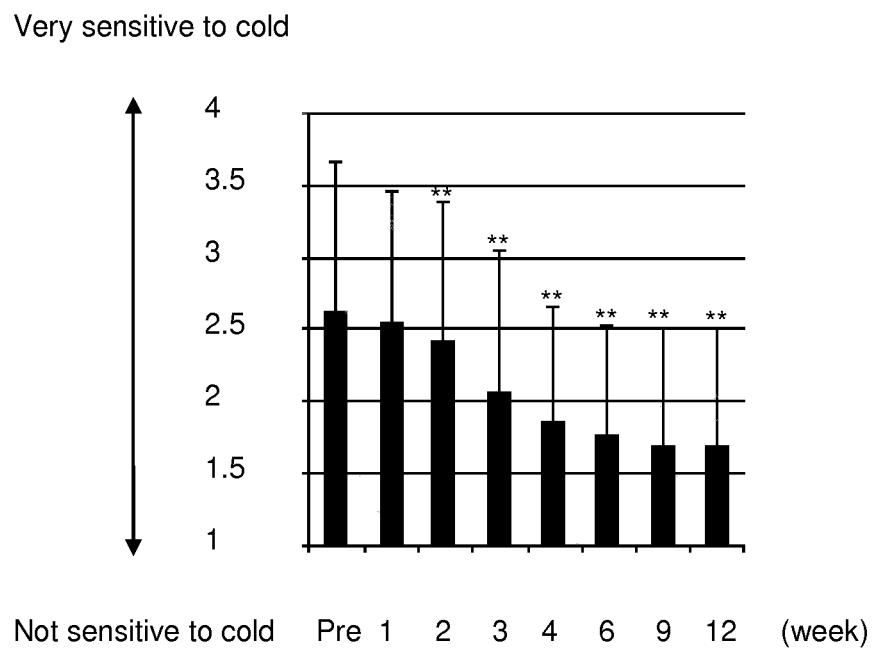
Fig. 1 THE EFFECT OF IMPROVING SENSITIVITY TO COLD
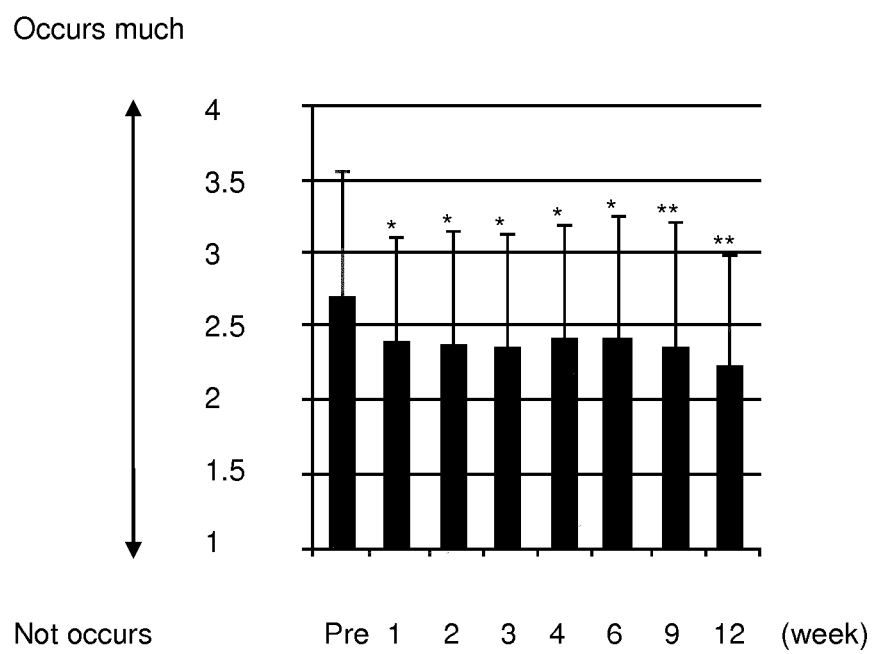
Fig. 2 THE EFFECT OF IMPROVING GENERAL FATIGUE Fig. 3 THE EFFECT OF IMPROVING GENERAL WEARINESS
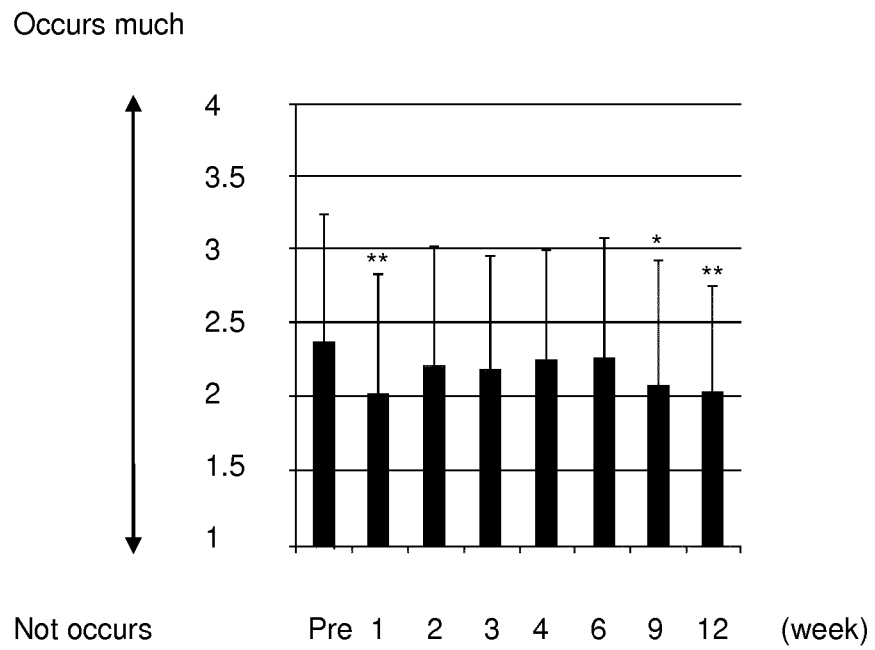
Fig. 4 IMPROVING STIFF SHOULDERS OR NECK STIFFNESS
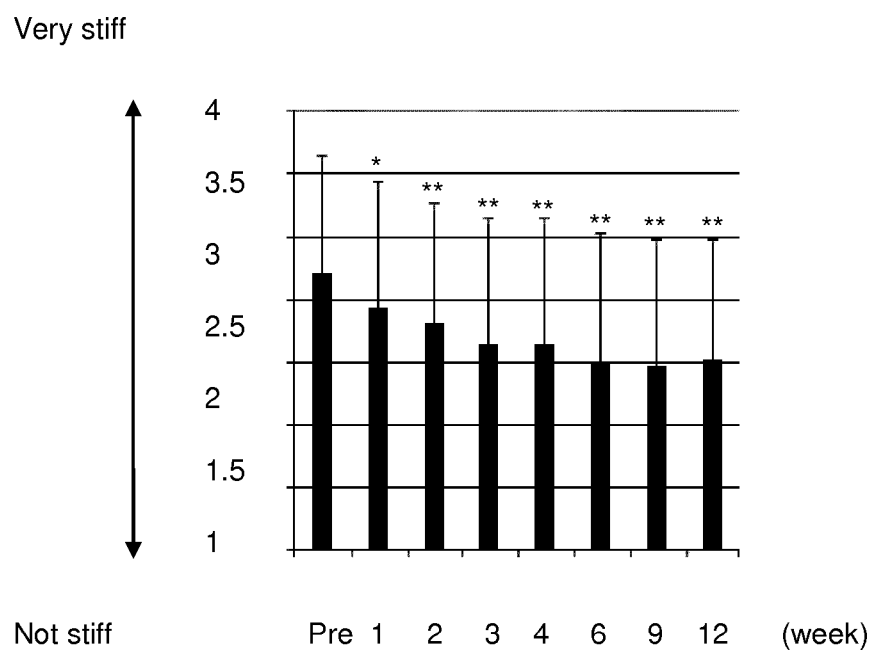

ORAL COMPOSITION FOR IMPROVING SYSTEMIC SYMPTOMS INCLUDING SENSITIVITY TO COLD

TECHNICAL FIELD

The present invention relates to an oral composition for improving systemic symptoms such as sensitivity to cold.

RELATED ART

Sensitivity to cold accompanies not only a symptom of chilled hands and legs but also systemic symptoms such as headaches and stiff shoulders. As is known in the art, sensitivity to cold is another phrase for the medical condition of cold hypersensitivity, which is defined as an excess autonomic nervous system reaction to low ambient temperature, characterized by bradycardia and a local wheal-and-flare reaction" (see, medical-dictionary.thefreedictionary.com/cold+hypersensitivity). Although bathing, dieting, physical exercise, and sleeping are suggested to cope with or treat this sensitivity to cold, only insufficient effect has been obtained so far. Also, vitamin compounds, herbal medicines, and the like besides sleep and diet therapies are used for systemic symptoms such as general fatigue and general weariness. However, it is hard to say that a sufficient effect is obtained. Also, bathing, dieting, massaging, anti-inflammatory agents, vitamin compounds, and herbal medicines are used for stiff shoulders or neck stiffness. However, the anti-inflammatory agents produce side effects such as gastric injuries and other measures have failed to obtain sufficient effects.

In the meantime, a red vine leaf extract is known to have an effect of improving swollen legs and symptoms associated with the swollen legs, for example, feelings of weariness, sluggishness, fatigue, tension, heat, and itching and put on the market as a medicine (trade name: Antistax, manufactured by SSP Co., Ltd.). However, this medicine is limited to symptoms of swollen legs and symptoms of legs by its indication and usage and its effect on systemic symptoms has been unknown at all.

Prior Art Document

[Non-Patent Document 1] A pamphlet of Antistax (SSP Co., Ltd.,)

SUMMARY OF THE INVENTION

It is an object of the present invention to provide a composition for safely and efficiently improving systemic symptoms such as sensitivity to cold, general fatigue, general weariness, and stiff shoulders or neck stiffness.

In light of this, the inventors of the present invention orally administered a red vine leaf extract to patients who were in mild abnormal venous return with swollen legs (for example, a calf and an ankle) and feelings of weariness, sluggishness, tension, and pain associated with the swollen legs, and unexpectedly found that not only swollen legs but also sensitivity to cold, general fatigue, general weariness, and stiff shoulders, and neck stiffness could be improved, to complete the present invention.

Accordingly, there are provided the following inventions <1> to <8>.

<1> An oral composition including a. red vine leaf extract as an effective component for improving a symptom selected from the group consisting of sensitivity to cold, general fatigue, general weariness, and stiff shoulders or neck stiffness. <2> The oral composition according to the above <1>, wherein the red vine leaf extract is an extract obtained by extracting a red vine leaf containing 0.2% by mass or more of anthocyan and 4% by mass or more of total polyphenols with water. <3> The oral composition according to the above <1> or <2>, wherein the red vine leaf extract contains 2 to 25% by mass of total flavonoids. <4> The oral composition according to any one of the above <1> to <3>, the composition being administered in a dose of 80 to 1000 mg per day in terms of solid content of the red vine leaf extract. <5> The oral composition according to any one of the above <1> to <4>, the composition being administered once a day. <6> The oral composition according to any one of the above <1> to <5>, wherein the leaf extract of red wine tree is a mixture containing a red vine leaf extract (solid content):silicon dioxide:glucose syrup (as dried glucose)=80:3:17 (ratio by mass). <7> The oral composition according to any one of the above <1> to <6>, the composition being used as a medicine. <8> The oral composition according to any one of the above <1> to <6>, the composition being used as a health food. Effects of the Invention When the composition of the present invention is orally administered, for example, once a day, the effect of improving subjective symptoms of systemic symptoms such as sensitivity to cold, general fatigue, general weariness, and stiff shoulders and neck stiffness is obtained.

BRIEF DESCRIPTION OF DRAWING

FIG. 1 is a view showing the effect of improving sensitivity to cold;

FIG. 2 is a view showing the effect of improving general fatigue;

FIG. 3 is a view showing the effect of improving general weariness; and

FIG. 4 is a view showing the effect of improving stiff shoulders or neck stiffness.

DETAILED DESCRIPTION OF THE INVENTION

The effective component of the oral composition for improving systemic symptoms of the present invention is a red vine leaf extract. The red vine leaf to be used as the raw material to be extracted is also called "dyer", which is a leaf of a grape (vitis vinifera LINNE) having a blackish blue pericarp and red fresh pulp. Any red vine leaf may be used regardless of the kind of grape.

The concentration of various polyphenol compounds in a red vine leaf and their structures are affected by various environmentally physiological factors at places where plants grow. In the present invention, it is preferable to use a red vine leaf containing 0.2% by mass or more of anthocyan and 4% by mass or more of total polyphenols as starting material. Here, the anthocyan includes anthocyanidin and its glycoside, namely, anthocyanin. Also, the total polyphenols are a generic name of various types of polyphenols. The red vine leaves having such characteristics are red vine leaves collected when the content of flavonoid reaches an optimum level, that is, red vine leaves generally collected at the time near to the vine fruit harvest season. Also, it is preferable to use a red vine leaf having a length of 15 cm or less and a width of 12 cm or less. The red vine leaves are preferably dried and ground upon use. The leaves to be used for the extraction are preferably cut into 10-mm-long pieces.

The red vine leaf extract used in the present invention is preferably an aqueous extract from red vine leaves and more preferably an extract obtained from red vine leaves by extraction with water.

The extraction is carried out at a temperature range from, preferably, 60° C. to 80° C. for at least 6 hr to 10 hr by using purified water to achieve a high flavonoid yield. The extraction method is preferably an exhaustive percolation. In this case, a so-called liquid extract obtained in the course of extraction may be used directly for the preparation of a liquid dosage form.

In order to obtain a more concentrated one as the extract, it is preferable to remove at least a part of the solvent by using an appropriate evaporator. The concentrated extract is made to stay under a heating and pressure condition, preferably at 120 to 150° C. for 1 to 30 seconds and more preferably at 140 to 145° C. for 2 to 5 seconds to carry out sterilization treatment. The concentrated extract obtained in this process may also be directly used for the preparation of the liquid dosage form.

The concentrated extract is dried by using, for example, a vacuum drying oven or vacuum drying conveyer to prepare a solid dosage form. An excipient may be added to the extract in the drying process to make easy the subsequent treatment. Examples of this excipient may include one or two or more types selected from silicon dioxide, maltodextrin, glucose syrup, cellulose, and the like. It is preferable to use one or two types selected from silicon dioxide and glucose syrup in the present invention. As to the amount of the excipient to be added, though no particular limitation is imposed on it, it is preferable to add 3% by mass of silicon dioxide and 17% by mass of glucose syrup (as a dry product) based on 80% by mass of the red vine extract (in terms of solid content) in the red vine leaf extract mixture (hereinafter this mixture is referred to as a red vine leaf extract mixture).

The red vine leaf extract used in the present invention is one containing total flavonoid (as quercetin-3-0-β-D-glucuronide) in an amount of, preferably 2 to 25% by mass, more preferably 2. 5 to 12.5% by mass, and even more preferably 2.75 to 8.25% by mass based on a pure extract (solid content) of the red vine leaf extract. As to the content of this total flavonoid in a red vine leaf extract containing a red vine leaf extract mixture (a solid substance containing 80% by mass (as solid content) of a red vine extract, 3% by mass of silicon dioxide, and 17% by mass of glucose syrup (as a dry product), a red vine extract containing 1.6 to 20%, preferably 2 to 10%, and more preferably 2.2 to 6.6% by mass of total flavonoid (quercetin-3-0-β-D-glucuronide) is used.

The dose of the red vine extract to be used for the oral composition for improving systemic symptoms of the present invention is usually in a range from 64 to 800 mg, preferably 240 to 640 mg, and more preferably 280 to 600 mg, and even more preferably 360 mg based on the red vine extract (solid content) per day for an adult.

The dose of the red vine leaf extra mixture is usually in a range from 80 to 1000 mg, preferably 300 to 800 mg, more preferably 350 to 750 mg, and even more preferably 450 mg based on the red vine extract mixture per day for an adult.

The oral composition for improving systemic symptoms of the present invention is orally taken. The composition is taken preferably once a day. The composition is more preferably taken once a day in the morning and particularly before breakfast. The regulation of the amount of an active component may reflect the age, weight, and manifest symptoms. the composition of the present invention may contain other active components besides the above red vine leaf extract.

The oral composition for improving systemic symptoms may be used for various types of preparations for oral administration, for example, a tablet, granule, fine granule, powder, capsule, caplet, soft capsule, pill, internal liquid, drink, jelly, syrup, dry syrup, chewable agent, troche, effervescent tablet, drop, suspension, and orally disintegrating tablet. These dosage forms may be produced by a usual method. Besides the aforementioned ingredients, any excipient which can be usually used may be added as required to these preparations. Moreover, the composition may be made into the aforementioned preparations after it is made into microparticles such as a microcapsule, nanocapsule, microsphere, nanosphere, ribosome or the like.

The red vine leaf extract may be made into a dosage form such as an individual granule, multilayer granule, multilayer tablet, or dry coated tablet, tablet of different granules, microcapsule, or the like. The red vine leaf extract may also be made into dosage forms including coating preparations such as a sugar-coated tablet, film-coating tablet, or coating granule in the same manner as in the case of dosage forms such as a chewable tablet, orally disintegrating tablet, matrix tablet, matrix granule, effervescent tablet, coground agent, and solid solution form. These methods may be combined. Moreover, the characteristics of the oral composition of the present invention are featured by improvements in stability, releasability, long-lasting ability, disintegrating ability, solubility, taste masking ability, and dosage and these characteristics can be controlled by adding additives known in the technical field concerned.

The oral dosage form of the composition of the present invention may be produced by adding usual medical additives and food additives, for example, an excipient, binder, disintegrating agent, lubricant, coating agent, sugar-coating agent, plasticizer, anti-foaming agent, glazing agent, foaming agent, antistatic agent, desiccant, surfactant, solubilizer, buffering agent, resolvent, solubilizing aid, solvent, diluent, stabilizer, emulsifier, suspension, suspending agent, dispersant, tonicity agent, adsorbent, reducing agent, antioxidant, moisturizing agent, moisture conditioning agent, filler, extender, adhesive, thickener, softening agent, pH regulator, antiseptic, preservative, sweetener, corrigent, coolant, seasoning, perfume, aromatic, and colorant, to the effective component according to usual methods. Examples of these additives are described in Japanese Pharmaceutical Excipients Directory 2007 (Edited by International Pharmaceutical Excipients Council Japan, YAKUJI NIPPO LIMITED) and JAPANS SPECIFICATIONS AND STANDARDS FOR FOOD ADDITIVES Eighth edition (Japan Food Additives Association).

The composition may further contain other components. There is no particular limitation to these other components as long as they are admitted in final dosage forms such as drink and food products and medicines and can be orally administered.

When the composition of the present invention is orally administrated, the oral composition for improving systemic symptoms of the present invention may be used as health food product compositions or medical product compositions which can improve systemic subjective symptoms such as sensitivity to cold, general fatigue, general weariness, and stiff shoulders and neck stiffness.

EXAMPLES

The present invention will be explained in more detail by way of examples. However, these examples are not intended to be limiting of the present invention.

Example 1

Production of a Capsule Agent

The following components were prepared into a filler powder by a usual method and filled in an amount of 247 mg in a capsule.

TABLE 1

| | |
|---|---|
| Red vine leaf extract mixture | 4500 g |
| Corn starch | 168 g |
| Talc | 168 g |
| Light anhydrous silicic acid | 52 g |
| Magnesium stearate | 52 g |

(Red vine leaf extract mixture~Aqueous extract from dry red vine leaf (solid content): silicon dioxide:glucose syrup (as dry glucose) = 80:3:17 in a ratio by mass)

Test Example 1

Subjects

Total 50 subjects consisting of 10 adult men and 40 adult women who are 20 to so years old and have symptoms including sensitivity to cold (cold hands and feet}, general fatigue, general weariness, stiff shoulders, and neck stiffness besides each symptom associated with swollen legs.

(Method)

Using the capsule agent of Example 1, two capsules were administered to each subject in the morning once a day for 12 weeks. The effect of improving each symptom in 37 examples of sensitivity to cold, 44 examples of general fatigue, 3 9 examples of general weariness, 46 examples of stiff shoulders or neck stiffness was determined by the results of questionnaires. The questionnaire was conducted in the following methods. The background of the object was surveyed and the condition of the object before the medicine was taken was confirmed using a questionnaire method. Also, the conditions of each subject 1 week, 2 weeks, 3 weeks, 4 weeks, 6 weeks, 9 weeks, and 12 weeks after the start of administration, that is, conditions at a total of B different times were measured using a questionnaire method to evaluate the sensation in the use of the test medicine for each symptom after the test medicine was administered since the start of administration. In the questionnaire method on the questionnaire sheet, the evaluation was made according to the four-grade system: 1: "Occurs much", 2: "Occurs a little", 3: "Somewhat occurs", and 4: "Not occurs" in correspondence with each of the following questions: for example, "Do you have a symptom of swollen legs?", "Do you have a symptom of general fatigue?", and "Do you have a symptom of sensitivity to cold?". The definition of each grade was optionally changed as follows corresponding to the item of the question: for example, "Occurs much" was changed to "Very sensitive to cold" and "very stiff". Also, to evaluate the medicine as to the sense of use for other symptoms, a survey was conducted using a questionnaire sheet method after the medicine was administered. Moreover, for example, diseases and injuries that occurred while the test medicine was administered, whether or not some treatment was performed, whether or not some drugs were administered, whether or not the administration of the test medicine was forgotten, and whether or not the test medicine was excessively administered were investigated using the patient diary.

(Results)

The results are shown in FIGS. 1 to 4. As is clear from FIGS. 1 to 4, a significant improving effect was produced by administrating a red vine leaf extract in all symptoms of sensitivity to cold, general fatigue, general weariness, stiff shoulders, and neck stiffness.

What is claimed is:

1. A method of treating hypersensitivity to cold, comprising orally administering to a patient suffering from systemic, non-localized hypersensitivity to cold an effective amount of a composition comprising a red-vine-leaf (folia *vitis viniferae*) extract,
   wherein the extract is obtained by extracting with water from a source material of red-vine-leaf containing at least 0.2% by mass of anthocyan and at least 4% by mass of total polyphenols, and
   wherein the extract contains 2 to 25% by mass of total flavonoids.

2. The method according to claim 1, the composition being orally administered in a dose of 80 to 1000 mg per day in terms of solid content of the red vine leaf extract.

3. The method according to claim 1, the composition being orally administered once a day.

4. The method according to claim 1, wherein the composition comprises the red- vine-leaf extract, silicon dioxide and dried glucose syrup at a dried solid mass ratio of 80:3:17.

* * * * *